(12) United States Patent
Vitrant et al.

(10) Patent No.: US 7,078,564 B2
(45) Date of Patent: Jul. 18, 2006

(54) PROCESS FOR THE PREPARATION OF ωBENZYL ESTERS OF AMINO DIACIDS AND OF ALKANESULPHONATES OF THESE ESTERS, AND THESE ALKANESULPHONATES

(75) Inventors: Anne Marie Vitrant, Itteville (FR); Laurence Ferruccio, Vert le Grand (FR); Charles-Henry Vincent, Precy sur Oise (FR)

(73) Assignee: Isochem (FR)

( * ) Notice: Subject to any disclaimer, the term of this patent is extended or adjusted under 35 U.S.C. 154(b) by 42 days.

(21) Appl. No.: 10/740,206

(22) Filed: Dec. 17, 2003

(65) Prior Publication Data

US 2004/0133033 A1 Jul. 8, 2004

(30) Foreign Application Priority Data

Dec. 20, 2002 (FR) .............................. 02 16344

(51) Int. Cl.
*C07C 229/00* (2006.01)

(52) U.S. Cl. ........................................ 562/433; 562/400
(58) Field of Classification Search ................ 562/433, 562/400
See application file for complete search history.

(56) References Cited

PUBLICATIONS

Rapoport et al, J. Org. Chem., 55, pp3068–3074.*
Clayton et al, Peptides, Journal Chemical Society, 1956, pp371–380.*

Clayton et al "Peptides. Part V . . . Peptide Chain", Journal Chemical Society, 1956, pp. 371–380, XP002254230.

Stein et al, "Enzyme–Catalyzed . . . Diesters", Journal of Organic Chemistry, vol. 60, No. 24, 1995, pp. 8110–8112, XP 002254231.

* cited by examiner

*Primary Examiner*—Cecilia J. Tsang
*Assistant Examiner*—Hector M. Reyes
(74) *Attorney, Agent, or Firm*—Charles A. Muserlian

(57) ABSTRACT

The invention relates to a process for the preparation of an ω-benzyl ester of an amino diacid, characterized in that the amino diacid is reacted with a benzyl alcohol derivative of formula (I)

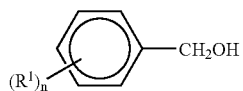

in which the $R^1$ substituent or substituents, which are identical or different, represent a hydrogen atom, a $C_1$ to $C_4$ alkyl group, a $C_1$ to $C_4$ alkoxy group or a halogen atom and n is equal to 1, 2 or 3, in the presence of at least one mol per mole of the amino diacid of an alkanesulphonic acid, optionally in the presence of a solvent.

The intermediate alkanesulphonates of the ω-benzyl esters of amino diacids and the ω-benzyl esters of amino diacids are obtained with a good yield and an excellent purity by virtue of this process.

21 Claims, No Drawings

PROCESS FOR THE PREPARATION OF ωBENZYL ESTERS OF AMINO DIACIDS AND OF ALKANESULPHONATES OF THESE ESTERS, AND THESE ALKANESULPHONATES

The invention relates to a process for the preparation of ω-benzyl esters of amino dicarboxylic acids, to a process for the preparation of the alkanesulphonates of these esters and to the alkanesulphonates of these esters themselves.

The ω-benzyl esters of amino diacids and their sulphonates, in particular those of aspartic and glutamic acids or their derivatives, are very useful compounds in the preparation of products intended for medicinal purposes and for agriculture.

Processes for the preparation of these compounds have been described. They consist in particular in reacting the amino diacid with benzyl alcohol or one of its derivatives in the presence of an acid.

However, none of these processes is truly satisfactory. The yields are often low and the esters still contain numerous impurities which render then unusable without subsequent purification treatments. In many cases, the diester or the α ester are formed predominantly. Furthermore, racemization frequently occurs and the desired L or D derivative is not obtained.

The use of concentrated sulphuric acid has been tried but is not suitable. When the acid is concentrated, the reaction takes place with a high exothermicity which is uncontrollable. The formation of benzyl alcohol polymers is also observed. When the acid is dilute, the equilibrium of the reaction is not favourable to the esterification. If sulphuric acid is replaced by hydrochloric acid, benzyl chlorides are predominantly formed.

Other acids have been employed, such as benzenesulphonic acid and para-toluenesulphonic acid, as mentioned by D. W. Clayton et al. in the journal J. Chem. Soc., 1956, p. 374. The reaction is generally carried out at high temperature with a large excess of benzyl alcohol or one of its derivatives. The excess benzyl alcohol and the operating conditions used bring about numerous side reactions, in particular the formation of the diester, and result in significant racemization.

Consequently, the problem of economically producing ω-benzyl esters of amino diacids on an industrial scale with a good yield, an excellent optical purity and by means of simple operations remained to be solved.

In accordance with the present invention, the problem is solved by reacting an amino dicarboxylic acid with a benzyl alcohol derivative of formula (I)

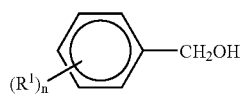

in which the $R^1$ substituent or substituents, which are identical or different, represent a hydrogen atom, a $C_1$ to $C_4$ alkyl group, a $C_1$ to $C_4$ alkoxy group or a halogen atom and n is equal to 1, 2 or 3, in the presence of at least one mol per mole of the amino dicarboxylic acid of an alkanesulphonic acid, optionally in the presence of a solvent.

By virtue of this process, the ω-benzyl esters of the amino diacids and, as intermediates, the alkanesulphonates of these esters are obtained in a simple way with good yields and with a high chemical and optical purity, these purities generally being greater than 99%.

The amino dicarboxylic acids of advantage as starting compounds are in particular the amino dicarboxylic acids used in the field of peptides. The radical carrying the two carboxyl groups and the amino group can be highly varied and in particular can be an aliphatic, cycloaliphatic, aryl, araliphatic or heterocyclic radical or a radical composed of several of these radicals. It is unsubstituted or substituted, in particular by the usual substituents of amino acids. The substituents are protected, if necessary.

The amino diacids can be natural or unnatural and occur in nature or are obtained by synthesis.

In particular, they are the amino diacids for which the two carboxylic acid functional groups are not attached to the same carbon atom or are not attached to the molecule symmetrically with respect to the group

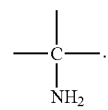

The amino group of the amino diacids can be protected by one of the usual protective groups for the amino group, such as those used in peptide chemistry, provided that this protective group is removed under the acidic conditions of the reaction. Mention may be made, as protective group, for example, of the tert-butyloxycarbonyl (BOC) group.

In particular, the amino diacids are the natural or unnatural α-amino carboxylic acids carrying another carboxyl group situated on a carbon other than that in the α position, in their various forms. Mention may in particular be made of aspartic acid, glutamic acid and the derivatives of these acids.

The amino diacids are esterified in their optically active D or L form to produce the corresponding D or L ω-benzyl esters virtually without racemization and with good yields, the esterification taking place mainly on the carboxyl group situated in the ω position.

Racemic ω-benzyl esters can also be obtained from the corresponding racemic amino diacids.

The benzyl alcohol derivatives which are reacted with the amino diacids are the derivatives of formula (I)

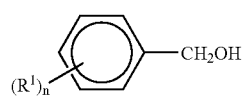

in which $R^1$ and n have the meaning indicated above.

When n is greater than 1, the $R^1$ substituents can be identical or different. n is preferably equal to 1 or 2. When $R^1$ represents a halogen atom, the latter is preferably chlorine or bromine.

Mention may in particular be made, as benzyl alcohol derivatives, of benzyl alcohols substituted by one or more alkyl groups, such as 4-methylbenzyl alcohol, 2,4-dimethylbenzyl alcohol, and the like, benzyl alcohols substituted by alkoxy groups, such as 4-methoxybenzyl alcohol, and the like, or benzyl alcohols substituted by halogen atoms, such as 3-chlorobenzyl alcohol, 2-bromobenzyl alcohol, and the like.

Preferably, the esterification is carried out with benzyl alcohol.

The amount of benzyl alcohol or of its derivative used is at least one mol per mole of amino diacid and preferably from 1.2 mol to 3 mol.

Contrary to the teaching of the prior art, it has been found that it is preferable to carry out the reaction with a slight excess of benzyl alcohol or of its derivative. The side reactions and the appearance of undesirable by-products are thus avoided.

The medium must, however, remain stirrable. If necessary, a solvent is then added to allow better stirring of the medium.

An acid must be present in the medium for esterification to take place. The acids used in the processes according to the prior art are not satisfactory. It has been found that, surprisingly, when an alkanesulphonic acid is used, the process according to the invention results in ω-benzyl esters with good yields and an excellent optical purity.

Mention may be made, as alkanesulphonic acids, of $C_1$ to $C_4$ alkanesulphonic acids and in particular methanesulphonic acid, ethanesulphonic acid or propanesulphonic acid. Preferably, methanesulphonic acid is used.

The reaction scheme from aspartic or glutamic acid, benzyl alcohol and methanesulphonic acid is as follows:

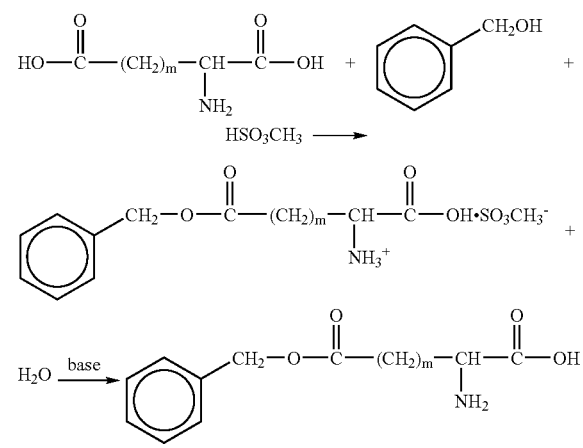

m = 1 or 2

The necessary amount of alkanesulphonic acid to be added is at least one mol per mole of the amino diacid, in order to neutralize the amine functional group. Preferably, use is made of an excess of this sulphonic acid, in particular an amount of 1.01 to 2 mol per mole of the amino diacid and more particularly of 1.05 to 1.2 mol. Alternatively, 1 mol of alkanesulphonic acid is added and the excess acid, i.e. from 0.01 to 1 mol, is introduced by adding another acid, such as, for example, sulphuric acid.

The constituents of the reaction mixture can be introduced in any order, depending on the stirrability of the medium. It is thus possible to mix first the amino diacid with the alkanesulphonic acid in the presence of a solvent and then to add, to the medium, the benzyl alcohol derivative. In some cases, it is preferable to mix the amino diacid, the benzyl alcohol or its derivative, and optionally the solvent and then to add, in particular gradually, the alkanesulphonic acid.

Mention may be made, as solvents which can be used, of aromatic or aliphatic and halogenated or nonhalogenated hydrocarbonaceous solvents, such as benzene, toluene, xylenes, chlorobenzene, cyclohexane, 1,2-dichloroethane, dichloromethane or chloroform.

The solvents which do not dissolve the alkanesulphonate of the ω-benzyl ester of the amino diacid are very suitable in particular. Those which also form a good azeotrope with water are also advantageous. Preferably, toluene is used.

The amount by volume (expressed in litres) of solvent when it is present is generally between 0.5 and 10 times the amount by weight (expressed in kg) of amino diacid used.

The temperature of the reaction varies according to the type of amino diacid to be esterified but it has been found that the results are markedly improved if the choice is made to maintain the temperature at values which are not excessively high, in particular less than or equal to 80° C. and more particularly of, from 30° C. to 50° C., when glutamic acid is used, and from 30 to 80° C., when aspartic acid is used.

The reaction time, for its part, varies in particular according to the temperature and the amino diacid to be esterified. It is generally between 1 hour and 24 hours.

The reaction results in the formation of the ω-benzyl ester of the amino diacid in the form of the salt of the alkanesulphonic acid.

Furthermore, it has been found that the yield of the process and the purity of the ω-benzyl ester are further increased if the said alkanesulphonic salt of the ω-benzyl ester is completely crystallized before carrying out the operations of recovery of the ester in the free form.

To do this, when a solvent has been used, the distillation of the solvent/water azeotrope is preferably carried out. This distillation is generally carried out continuously as the reaction progresses. If necessary, it is carried out under a reduced pressure in order to keep the temperature of the reaction medium within the limits indicated above, in particular at a value of less than or equal to 80° C.

Optionally, the medium is subsequently cooled in order for the crystallization of the alkanesulphonate of the ω-benzyl ester to be truly complete. The alkanesulphonate obtained can be isolated, for example by filtration. It can also be rinsed with an organic solvent which does not dissolve it, such as the solvent used in the reaction, in particular with toluene, to complete the removal of the impurities.

When no solvent is used or when a small amount of solvent is present in the medium, it is preferable to crystallize the alkanesulphonate directly. Generally, the medium is cooled. Optionally, other known techniques, such as seeding, can be used. Preferably, the medium is cooled very slowly. Several hours may then be necessary.

The subject-matter of the present invention also relates to alkanesulphonate salts of o)-benzyl esters of amino dicarboxylic acids. These are novel compounds.

The various parts: benzyl residues, amino diacid residues and alkanesulphonic acid residues, which constitute these salts originate in particular from the benzyl alcohol or from its derivatives of formula (I) and from the amino diacids and from the alkanesulphonic acids as described above. They can be in the optically active form, such as D or L, or in the racemic form.

In particular, the benzyl residue results from benzyl alcohol, the amino dicarboxylic acid residue results from an α-amino carboxylic acid carrying another carboxyl group attached to a carbon other than that in the α position, and the alkanesulphonic acid residue results from a $C_1$ to $C_4$ alkanesulphonic acid, more particularly from methanesulphonic acid.

They can be represented by the following formula (II):

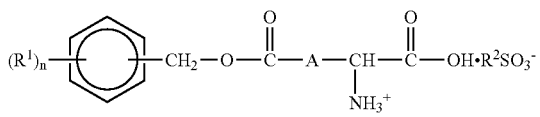

in which $R^1$ and n are as defined for the formula (I), A is the part of the molecule of an α-amino carboxylic acid attached to the carbon in the α position and to the carboxyl group in the ω position, and $R^2$ represents the alkane residue of the alkanesulphonic acid.

$R^1$ is preferably a hydrogen atom and $R^2$ is preferably a $C_1$ to $C_4$ alkane residue, in particular the $CH_3$ radical.

Mention may in particular be made, as examples of such salts, of γ-benzyl glutamate methanesulphonate and β-benzyl aspartate methanesulphonate, in particular in their L or D form.

These salts are obtained by the process of the present invention as described above, with an excellent chemical and optical purity.

When it is wished to recover the ω-benzyl ester no longer in its alkanesulphonic salt form but in its free form, the alkanesulphonate of the ω-benzyl ester, optionally after having been dissolved in water, is brought into contact with an organic or inorganic base, such as, for example, an aqueous ammonia solution, an aqueous alkali metal hydroxide solution or an aqueous alkali metal carbonate solution, such as an aqueous solution of sodium hydroxide or of a sodium carbonate. Preferably, an aqueous ammonia solution is used.

In particular, the base is added in an amount sufficient to bring the pH of the medium to and to maintain it at the isoelectric point of the ester to be produced or more particularly to bring the pH of the medium to and to maintain it at a value of 6 to 7 for aspartic acid or glutamic acid.

The free ester precipitates as the pH is raised to the value of the isoelectric point. It is then easily recovered in a conventional way, for example by filtration.

It has been found that the purity of the free ester is further improved by removing the impurities in the following way. After having crystallized the alkanesulphonate of the ω-benzyl ester, preferably slowly, it is not isolated but is dissolved with water and is treated with a base as indicted above. Generally, water is added to the medium in an amount sufficient to dissolve it. Preferably, 2 to 3 volumes (in litres) of water are added with respect to the weight (in kg) of the amino diacid involved or of the alkanesulphonate of the ω-benzyl ester. The organic phase is optionally removed by separation by settling. The organic or inorganic base, preferably an aqueous ammonia solution, is added with the water or afterwards in order to reach the pH of the isoelectric point and the procedure is carried out as described above.

According to a preferred alternative form, the subsequent operations of filtering and of washing the free ester are facilitated and, for this reason, the impurities are removed even better by heating the medium, after having reached the pH of the isoelectric point, preferably at a temperature of between 50° and 70° C. The ester is subsequently precipitated, for example by cooling.

For an even higher purity, a solvent for benzyl alcohol or for its derivative, for example an alcohol, such as methanol, ethanol or isopropanol, an ester or a ketone, can be added to the medium comprising the ester to be released, generally in an amount of between 1 and 10 volumes (in litres), in particular between 3 and 5 volumes, with respect to the weight (in kg) of amino acid used. Preferably, this solvent is added with the water or after the introduction of the water, optionally with the base.

The yields of ω-benzyl esters obtained are markedly improved with respect to those of the prior art. The chemical and optical purity of these esters is excellent, greater than 99%.

The examples which follow illustrate the invention without, however, limiting it.

EXAMPLE 1

Preparation of γ-benzyl Glutamate 1 kg (6.79 mol, 1 eq.) of L-glutamic acid, 1.1 kg (10.17 mol, 1.5 eq.) of benzyl alcohol and 1 litre of toluene are introduced into a fitted-out 5.2 litre reactor and the mixture is stirred. 0.784 kg (8.15 mol, 1.2 eq.) of methanesulphonic acid is subsequently introduced gradually while maintaining the temperature of the mixture at 45° C. Stirring of the mixture is continued at this temperature for a further 2 hours, then the mixture is cooled to 30° C.–32° C. and stirring is continued at 30° C.–32° C. for 4 hours.

2 litres of water are subsequently added. The organic phase and the aqueous phase are then separated by settling.

The aqueous phase collected is conveyed to another reactor. 3 litres of ethanol are then added to this phase, followed by 0.8 litre of 22° B aqueous ammonia to reach a pH of 6.5–7. The mixture is subsequently heated to 60° C. and is stirred at this temperature for 2 hours in order to improve the crystalline form of the product.

The mixture is cooled to a temperature of 5° C.–10° C. A crystalline solid precipitates. It is filtered off and washed twice with 1 litre of ethanol and 3 times with 1 litre of water.

A wet product is collected and is dried under vacuum. 1.25 kg (77% yield) of γ-benzyl L-glutamate are thus obtained, the characteristics of which are as follows:

$[\alpha]_D^{20}$: +19° (c=1, in acetic acid).
Melting point (M.p.): 167.5° C.
Purity by HPLC: 99.7%.
Diameter of the particles: 95.5 μm (for 90% of the particles).

In the same way, starting from D-glutamic acid, γ-benzyl D-glutamate was obtained, the characteristics of which are as follows:

$[\alpha]_D^{20}$: −19.5° (c=1, in acetic acid).
Purity by HPLC: 99%.

EXAMPLE 2

Preparation of γ-benzyl L-glutamate methanesulphonate and γ-benzyl L-glutamate 1 620 ml of toluene, 294 g (2 mol, 1 eq.) of L-glutamic acid and 648 g (6 mol, 3 eq.) of benzyl alcohol are introduced into a fitted-out and stirred 3 litre reactor and the mixture is heated to a temperature of 30° C.–35° C.

240 g (2.5 mol, 1.25 eq.) of 99% methanesulphonic acid are gradually added while maintaining the mixture at a temperature of 30° C.–35° C. The toluene/water azeotrope is distilled off at 30° C.–35° C. over 4 h 30 under a pressure of 38 to 47 mbar.

The medium is cooled to 15° C. The γ-benzyl L-glutamate methanesulphonate precipitates. It is filtered off and is rinsed several times with toluene. 653 g of wet γ-benzyl L-glutamate methanesulphonate are thus obtained in the form of a white crystalline powder, the characteristics of which in the dry state are as follows:
Melting point: 123.1° C.
$^1$H NMR (200 MHz, d$_6$-DMSO).
The protons are located by the FIGS. 1 to 9 on the formula below:

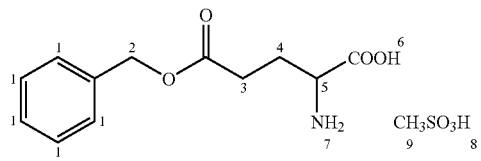

1: 7.35 ppm, 2: 5.1 ppm, 3: 2.6 ppm, 4: 2.05 ppm, 5: 3.95 ppm, 9: 2.35 ppm, mobile protons 8.3 ppm.

The wet γ-benzyl L-glutamate methanesulphonate obtained above is reintroduced into the reactor, which contains 1.8 litres of water, and a further distillation is carried out to remove the remainder of the toluene. 325 ml of a 10% w/w aqueous ammonia solution are subsequently added in order for the pH of the medium to be 6.1±0.2. The temperature of the medium is 13° C.–15° C. Stirring of the mixture is continued at this pH for 2 hours.

The precipitate is filtered off and is rinsed several times with water. It is dried in an oven at 45° C. 382.8 g (81% yield) of γ-benzyl L-glutamate are then recovered in the form of a white powder with the following characteristics:
$[\alpha]_D^{20}$: +20.8° (c=1, in acetic acid).
Purity determined by HPLC: 99.9%.
Percentage of L-glutamic acid by TLC analysis: <0.1%.
Diameter of the particles: 222.7 μm (for 90%).

EXAMPLE 3

Preparation of β-benzyl L-aspartate 100 g (0.75 mol, 1 eq.) of L-aspartic acid and 162 g (1.5 mol, 2 eq.) of benzyl alcohol are introduced into a fitted-out 1 litre reactor and the mixture is stirred. 86.4 g (0.9 mol, 1.2 eq.) of methanesulphonic acid are subsequently introduced gradually while allowing the temperature to rise. The temperature is brought by heating to 60° C., stirring of the mixture is continued for 12 hours and then the mixture is cooled to 40° C.

200 ml of water are subsequently added, then 300 ml of ethanol are added and subsequently 95 ml of 22° B aqueous ammonia are added, so as to precipitate the ester at a pH of 6.5–7.

The mixture is subsequently heated to 60° C. and is stirred at this temperature for 2 hours to improve the crystalline form of the product.

It is cooled to a temperature of 5° C.–10° C. The crystalline precipitate is filtered off and washed twice with 100 ml of ethanol and 3 times with 100 ml of water.

A wet product is collected and is dried under vacuum. 108 g (64% yield) of β-benzyl L-aspartate are thus obtained, the characteristics of which are as follows:
Appearance: white powder.
Melting point: 212° C.
$[\alpha]_D^{20}$: +27.6° (read at 1% in HCl 1N).
Purity determined by HPLC: >99.9%.

By carrying out the preparation in the same way from D-aspartic acid, β-benzyl D-aspartate is obtained.

EXAMPLE 4

Preparation of β-benzyl L-aspartate 532 g (4 mol) of L-aspartic acid, 665 ml of 1,2-dichloroethane (DCE), 665 ml of cyclohexane and 318 ml of 98% w/w methanesulphonic acid (MSA) diluted with 188.5 ml of water (i.e. 4.8 mol of MSA) are introduced into a fitted-out 4 litre reactor. 827 ml (8 mol) of benzyl alcohol are added to this medium.

The medium is heated to approximately 76° C. and the water/DCE/cyclohexane ternary azeotrope is distilled off. The precipitation of β-benzyl L-aspartate methanesulphonate is observed when 135 ml of water have been distilled off. The distillation lasts 10 hours. The temperature of the medium is close to 77° C. The total amount of water distilled off is 270 ml.

The medium is cooled to approximately 10° C., then it is filtered and the precipitate is rinsed with 2 times 530 ml of the DCE/cyclohexane (50/50) mixture.

After drying the precipitate, 861 g of solid white β-benzyl L-aspartate methanesulphonate are obtained (66% yield). It is dissolved in 3 volumes of water and then the pH is adjusted to 7±0.2 with 30% w/w sodium hydroxide solution. The precipitate is filtered off, rinsed with water and then dried in an oven under vacuum (45° C./20 mmHg). The yield of this second stage is 89% with respect to the benzyl aspartate methanesulphonate.

The purity of the β-benzyl aspartate, determined by HPLC, is 100%.

What is claimed is:

1. A process for the preparation of a salt of an ωester of an amino dicarboxylic acid, comprising A) reacting the ammo dicarboxyic acid with a benzyl alcohol derivative of the formula

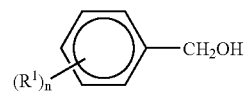

wherein R$^1$ is individually selected from the group consisting of hydrogen, C$_1$ to C$_4$ alkyl, C$_1$ to C$_4$ alkoxy and halogen and n is 1 or 3, in the presence of an alkanesulfonic acid catalyst with a molar ratio of at least one mole of catalyst per mole of the amino dicarboxylic acid, B) optionally in the presence of a solvent to obtain a salt thereof and optionally reacting the salt with a base to obtain the free form thereof.

2. The process of claim 1, wherein the amino dicarboxylic acid is an α-ammino carboxylic add carrying another carboxyl group attached to a carbon other than that in the α position.

3. The process of claim 2, wherein the amino dicarboxylic acid is glutamic acid or aspartic acid.

4. The process of claim 1 wherein the alcohol of formula (I) is benzyl alcohol.

5. The process of claim 1 wherein the temperature of the A) reaction is less than or equal to 80°C.

6. The process of claim 1 wherein the benzyl alcohol or its derivative of formula (I) is used in an amount of 1.2 to 3 mol per mole of the amino dicarboxylic acid.

7. The process of claim 1 wherein the alkanesulfonic acid is methanesulfonic acid.

8. The process of claim 1 wherein the amount of alkanesulfonic acid used is 1.01 to 2 mol per mole of the amino dicarboxylic acid.

9. The process of claim 1 wherein the solvent of the A) reaction is selected from the group consisting of aliphatic and aromatic and halogenated and nonhalogenated hydrocarbons.

10. The process of claim 1 wherein the ω-benzyl ester of the amino dicarboxylic acid is obtained in the free form by bringing the alkanesulfonate of the ω-benzyl ester of the amino dicarboxylic acid into contact with an organic or inorganic base.

11. The process of claim 10, wherein the base is used in an amount sufficient to reach the isoelectric point of the ester to be obtained.

12. The process of claim 10 wherein the base is an aqueous ammonia solution.

13. The process of claim 1 wherein the salt is crystallized before being converted to the free ω-benzyl ester of the amino dicarboxylic acid.

14. The process of claim 1 wherein a solvent/water azeotrope is distilled off the A) reaction at a temperature of less than 80° C.

15. The process of claim 1 wherein the salt is isolated before being brought into contact with the base.

16. The process of claim 1 wherein the salt is not isolated from the medium before this ester is released.

17. The process of claim 1 wherein the salt is dissolved in water.

18. The process of claim 17 wherein a solvent for the benzyl alcohol derivative is added with the water or after the introduction of water.

19. The process of claim 1 wherein, after having reached the pH of the isoelectric point of the A) reaction, the medium is heated.

20. Alkanesulfonate having the formula $$(R_1)_n\text{-Ar-}CH_2\text{-}O\text{-}\underset{O}{\overset{\|}{C}}\text{-}A\text{-}\underset{NH_3^+}{CH}\text{-}\underset{O}{\overset{\|}{C}}\text{-}OH \cdot R_2SO_3^-$$

wherein $R^1$ is hydrogen or is individually selected from the group consisting of $C_1$ to $C_4$ alkyl, $C_1$ to $C_4$ alkoxy and halogen, A is selected from the group consisting of an aliphatic, cycloaliphatic, aryl, araliphatic or heterocyclic and $R^2$ is alkane residue of the alkanesulfonic acid.

21. An alkanefulsonate of claim 20 wherein it is γ-benzyl glutamate methanesulfonate or β-benzyl aspirate methane sulfonate.

* * * * *